(12) United States Patent
Locke et al.

(10) Patent No.: US 12,414,719 B2
(45) Date of Patent: Sep. 16, 2025

(54) SEGMENTED ELECTRODE AND METHOD

(71) Applicant: Heraeus Medical Components LLC, St. Paul, MN (US)

(72) Inventors: Benjamin Locke, Lino Lakes, MN (US); Andres Campos, Racine, WI (US); Leroy G. Calander, Rush City, MN (US); Paul Noffke, St. Paul, MN (US); Daniel Nygaard, New Brighton, MN (US); Eric Eichelt, Balsam Lake, WI (US); Paul Schuster, St. Paul, MN (US); Mark A. Hjelle, White Bear Lake, MN (US); David Ohmann, Blaine, MN (US); John W. Warling, Maplewood, MN (US)

(73) Assignee: Heraeus Medical Components LLC, St. Paul, MN (US)

( * ) Notice: Subject to any disclaimer, the term of this patent is extended or adjusted under 35 U.S.C. 154(b) by 1015 days.

(21) Appl. No.: 15/677,723

(22) Filed: Aug. 15, 2017

(65) Prior Publication Data
US 2018/0042506 A1    Feb. 15, 2018

Related U.S. Application Data

(60) Provisional application No. 62/375,369, filed on Aug. 15, 2016.

(51) Int. Cl.
*A61B 5/287* (2021.01)
*A61N 1/05* (2006.01)
(Continued)

(52) U.S. Cl.
CPC ............... *A61B 5/287* (2021.01); *A61N 1/05* (2013.01); *A61N 1/37205* (2013.01);
(Continued)

(58) Field of Classification Search
CPC ..... A61B 5/0422; A61N 1/05; A61N 1/37205
See application file for complete search history.

(56) References Cited

U.S. PATENT DOCUMENTS

| 3,618,613 A | 11/1971 | Schulte |
| 4,610,674 A | 9/1986 | Suzuki et al. |

(Continued)

OTHER PUBLICATIONS

Connolly, Allison T. et al., "A Novel Lead Design for Modulation and Sensing of Deep Brain Structures," IEEE Transactions on Biomedical Engineering, vol. 63, No. 1, pp. 148-157 (Jan. 2016).
(Continued)

*Primary Examiner* — Jennifer Pitrak McDonald
*Assistant Examiner* — Jennifer L Ghand
(74) *Attorney, Agent, or Firm* — Dicke, Billig & Czaja, PLLC

(57) ABSTRACT

A medical lead for implantation includes an electrode assembly having a plurality of electrodes. Each of the plurality of electrodes include a plurality of electrode segments. Each electrode segment has a flexible conductor directly coupled to it. A strut is coupled within each of the plurality of electrodes such that each of the flexible conductors coupled to the plurality of electrode segments are supported between the strut and each of the plurality of electrodes by the strut. An insulator fills gaps between the plurality of electrodes, the strut and the flexible conductors.

14 Claims, 22 Drawing Sheets

(51) Int. Cl.
*A61N 1/372* (2006.01)
*B29C 45/14* (2006.01)
*H01R 24/58* (2011.01)
*H01R 43/24* (2006.01)
*A61B 5/00* (2006.01)
*B29L 31/00* (2006.01)
*H01R 13/58* (2006.01)
*H01R 107/00* (2006.01)

(52) U.S. Cl.
CPC ....... *B29C 45/14639* (2013.01); *H01R 24/58* (2013.01); *H01R 43/24* (2013.01); *A61B 5/686* (2013.01); *A61B 2562/0209* (2013.01); *A61B 2562/125* (2013.01); *A61B 2562/162* (2013.01); *B29L 2031/753* (2013.01); *H01R 13/5833* (2013.01); *H01R 2107/00* (2013.01); *H01R 2201/12* (2013.01)

(56) References Cited

U.S. PATENT DOCUMENTS

| | | | |
|---|---|---|---|
| 4,705,511 | A | 11/1987 | Kocak |
| 5,066,285 | A | 11/1991 | Hillstead |
| 5,167,647 | A | 12/1992 | Wijkamp et al. |
| 5,330,449 | A | 7/1994 | Prichard et al. |
| 5,380,301 | A | 1/1995 | Prichard et al. |
| 5,466,230 | A | 11/1995 | Davila |
| 5,507,732 | A | 4/1996 | McClure et al. |
| 5,599,325 | A | 2/1997 | Ju et al. |
| 5,935,159 | A | 8/1999 | Cross, Jr. et al. |
| 6,068,622 | A | 5/2000 | Sater et al. |
| 6,249,708 | B1 * | 6/2001 | Nelson ................... A61N 1/056 607/122 |
| 6,757,970 | B1 | 7/2004 | Kuzma et al. |
| 8,046,909 | B2 | 11/2011 | Dye et al. |
| 8,171,621 | B2 | 5/2012 | Swanson et al. |
| 8,225,504 | B2 | 7/2012 | Dye et al. |
| 9,054,436 | B2 | 6/2015 | Swanson et al. |
| 9,370,653 | B2 | 6/2016 | Sefkow et al. |
| 9,421,362 | B2 * | 8/2016 | Seeley ..................... A61N 1/05 |
| 2004/0019372 | A1 * | 1/2004 | Cole ......... A61N 1/05 607/116 |
| 2004/0097965 | A1 * | 5/2004 | Gardeski ........... A61M 25/0021 606/129 |
| 2009/0222073 | A1 * | 9/2009 | Flowers ............... A61N 1/3752 607/116 |
| 2010/0269337 | A1 * | 10/2010 | Dye ..................... A61N 1/0534 29/874 |
| 2011/0047795 | A1 | 3/2011 | Turner et al. |
| 2011/0313500 | A1 * | 12/2011 | Barker ................. A61N 1/0534 607/116 |
| 2012/0071949 | A1 * | 3/2012 | Pianca ..................... A61N 1/05 607/59 |
| 2012/0203320 | A1 * | 8/2012 | DiGiore ............... A61N 1/0534 607/148 |
| 2013/0109254 | A1 * | 5/2013 | Klardie ................ A61N 1/0534 439/887 |
| 2013/0274843 | A1 * | 10/2013 | Barker ................. A61N 1/0534 607/116 |
| 2013/0274844 | A1 * | 10/2013 | Leven .................. A61N 1/0551 607/116 |
| 2014/0130349 | A1 | 5/2014 | Swanson et al. |
| 2014/0309719 | A1 * | 10/2014 | Oster ....................... A61N 1/05 607/116 |
| 2015/0018915 | A1 * | 1/2015 | Leven ..................... A61N 1/05 607/116 |
| 2015/0021817 | A1 | 1/2015 | Romero et al. |
| 2015/0066120 | A1 | 3/2015 | Govea |

OTHER PUBLICATIONS

Teplitzky, Benjamin A. et al., "Model-Based Comparison of Deep Brain Stimulation Array Functionality with Varying Number of Radial Electrodes and Machine Learning Feature Sets," Frontiers in Computational Neuroscience, vol. 10, Article 58, pp. 1-5 (Jun. 10, 2016).

* cited by examiner

SEGMENTED ELECTRODE AND METHOD

CROSS REFERENCE TO RELATED APPLICATION

This Non-Provisional Patent Application claims the benefit of the filing date of U.S. Provisional Patent Application Ser. No. 62/375,369, filed Aug. 15, 2016, entitled "SEGMENTED ELECTRODE AND METHOD," which is herein incorporated by reference.

BACKGROUND

This disclosure relates to segmented electrodes configured for sensing and/or stimulation within a biological application. In some embodiments, ring electrodes are provided on the distal end of a lead for sensing or stimulation within a human body. The distal end of a lead is placed adjacent tissue that is to be sensed or stimulated and the ring electrodes either transmit or receive energy. In some cases, it is useful to have very discrete locations energized, and accordingly, use only a segment of a ring electrode, rather than the entire ring. Manufacturing discrete electrode segments can be difficult, particularly where multiple electrode segments are desired on a small diameter lead. For these and other reasons, there is a need for the present disclosure.

DETAILED DESCRIPTION

In the following Detailed Description, reference is made to the accompanying drawings, which form a part hereof, and in which is shown by way of illustration specific embodiments in which the embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the embodiments. The following detailed description, therefore, is not to be taken in a limiting sense, and the scope of the embodiments is defined by the appended claims.

Figure 1:
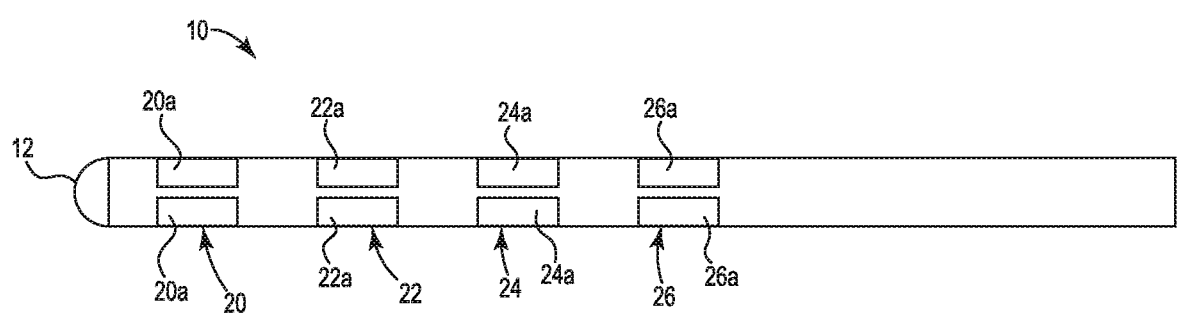
FIG. 1 illustrates a side view of a medical lead with segmented electrodes in accordance with one embodiment.

FIG. 1 illustrates a side view of a medical lead 10 with segmented electrodes 20, 22, 24, 26 in accordance with one embodiment. In one embodiment, lead 10 includes, adjacent its distal end 12, four electrodes 20, 22, 24, 26, each of which is segmented such that each has a plurality of individually accessible electrode segments. Specifically, first electrode 20 includes multiple electrode segments 20a; second electrode 22 includes multiple electrode segments 22a; third electrode 24 includes multiple electrode segments 24a; and fourth electrode 26 includes multiple electrode segments 240a. In one various embodiments, there are two, three, four or five electrode segments 20a, 22a, 24a, 26a, for each of electrodes 20, 22, 24, 26.

In operation, lead 10 may be configured for use within a human body. Once within a human body, each of electrode segments 20a, 22a, 24a, 26a may be used for directional stimulation or for positional feedback sensing. Rather than using a single ring electrode that spans the entire 360° circumference of the lead, lead 10 includes electrode segments 20a, 22a, 24a, 26a, which only span a portion of the circumference of lead 10 (for example, 180°, 90° degrees or less), such that directional stimulation or positional feedback sensing can be much more precisely controlled relative to a given target within the human body.

Furthermore, lead 10 in accordance with embodiments described herein, allow for the manufacture of leads having increased density of electrode segments. Increased density of electrode segments is useful in a variety of applications. For example, lead 10 can be used in deep brain stimulation (DBS), in which lead 10 delivers electrical pulses into one or several specific sites within the brain of a patient to treat various neurological disorders, such as chronic pain, tremors, Parkinson's disease, dystonia, epilepsy, depression, obsessive-compulsive disorder, and other disorders. In other applications, lead 10 may be configured for spinal cord stimulation, peripheral nerve stimulation, dorsal root stimulation, cortical stimulation, ablation therapies, cardiac rhythm management leads, various catheter configurations for sensing, and various other therapies where directional sensing or stimulation are needed.

Figure 2:
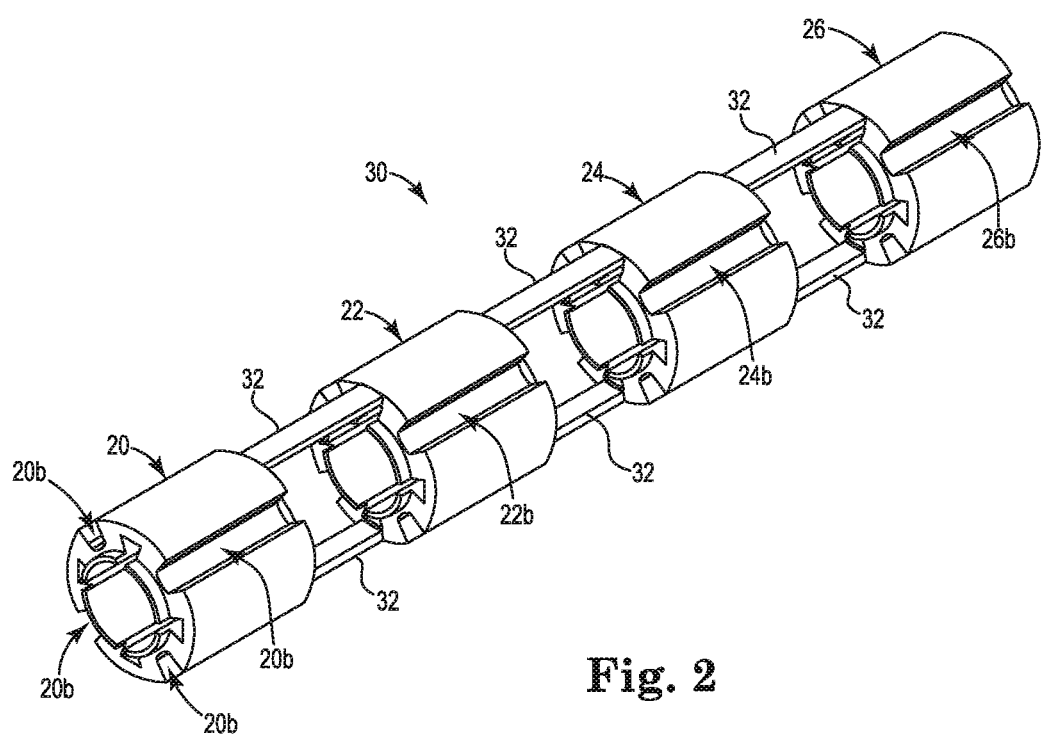
FIG. 2 illustrates a perspective view of an electrode assembly for a lead in accordance with one embodiment.

In one embodiment, the manufacture of lead 10 begins with electrode assembly 30, such as illustrated in FIG. 2. Electrode assembly 30 includes first electrode 20, second electrode 22, third electrode 24, and fourth electrode 26. Each electrode is coupled to at least on other electrode with coupling segments 32. Each electrode 20, 22, 24, 26 is provided with a plurality of grooves 20b, 22b, 24b, 26b, respectively, on the outer periphery of the electrode. The number of grooves provided in each electrode 20, 22, 24, 26 corresponds to the number of electrode segments 20a, 22a, 24a, 26a that will be provided for each electrode. A flexible conductor (not illustrated in FIG. 2) will be coupled within each groove 20b, 22b, 24b, 26b, thereby provided independent electrical access to each electrode segment 20a, 22a, 24a, 26a.

Electrode assembly 30 can be formed in a variety of way consistent with the embodiments. For example, electrode assembly 30 can be formed by machining, metal injection molding, 3-D printing and/or metal screen printing. Fabrication of electrode assembly 30 in this way simplifies the manufacturing process and provides precise and consistent electrodes. Forming electrode assembly 30 as a single part, with electrodes 20, 22, 24, 26 coupled together with coupling segments 32 also ensures that precise spacing between adjacent electrodes is maintained in the final lead 10, which can be important in many applications.

Figure 3:
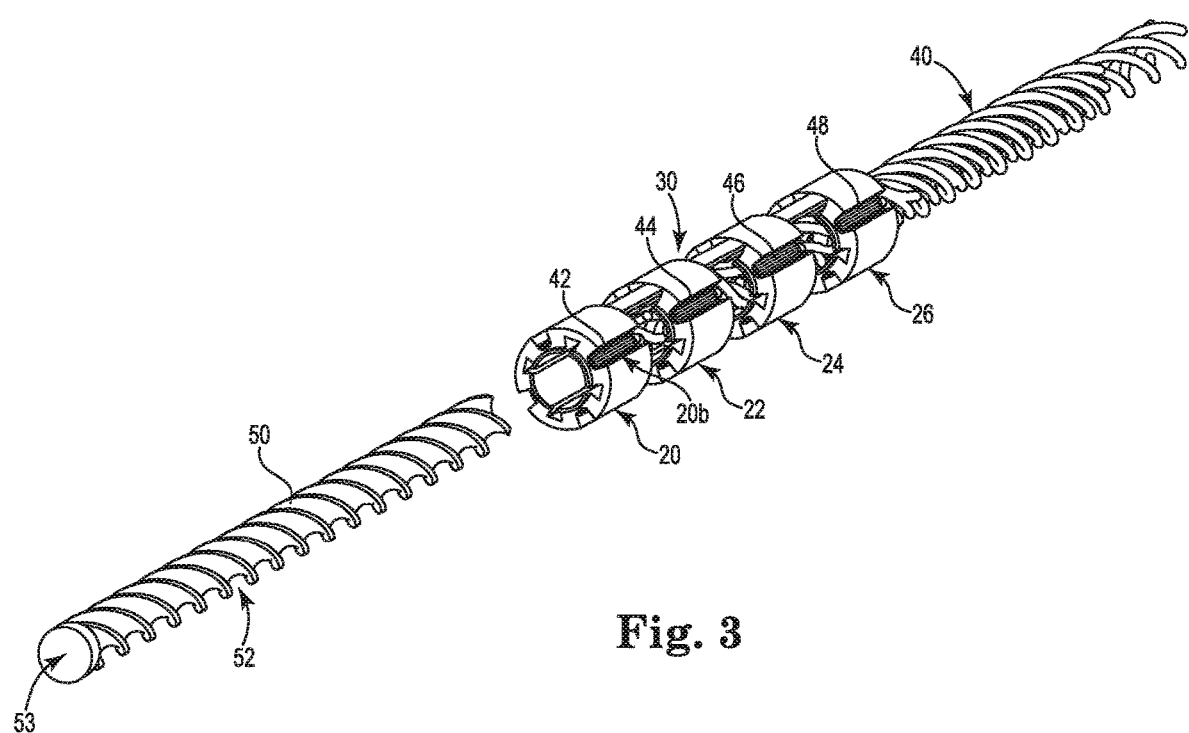
FIG. 3 illustrates an exploded perspective view of a strut and electrode assembly with wiring for a lead in accordance with one embodiment.

Electrode assembly 30 is illustrated in FIG. 3 coupled to a plurality of flexible conductors 40. Strut 50 is illustrated exploded away from electrode assembly 30. In one embodiment, a flexible conductor 42, 44, 46, 48 is placed in each groove 20b, 22b, 24b, 26b of each electrode 20, 22, 24, 26. For example, where each electrode 20, 22, 24, 26 includes four grooves 20b, 22b, 24b, 26b, the plurality of flexible conductors 40 includes a total of 16 flexible conductors. Once the plurality of flexible conductors 40 are coupled within the respective grooves 20b, 22b, 24b, 26b, strut 50 is placed within electrode assembly 30, thereby supporting the plurality of flexible conductors 40 between strut 50 and electrode assembly 30.

Figure 4:
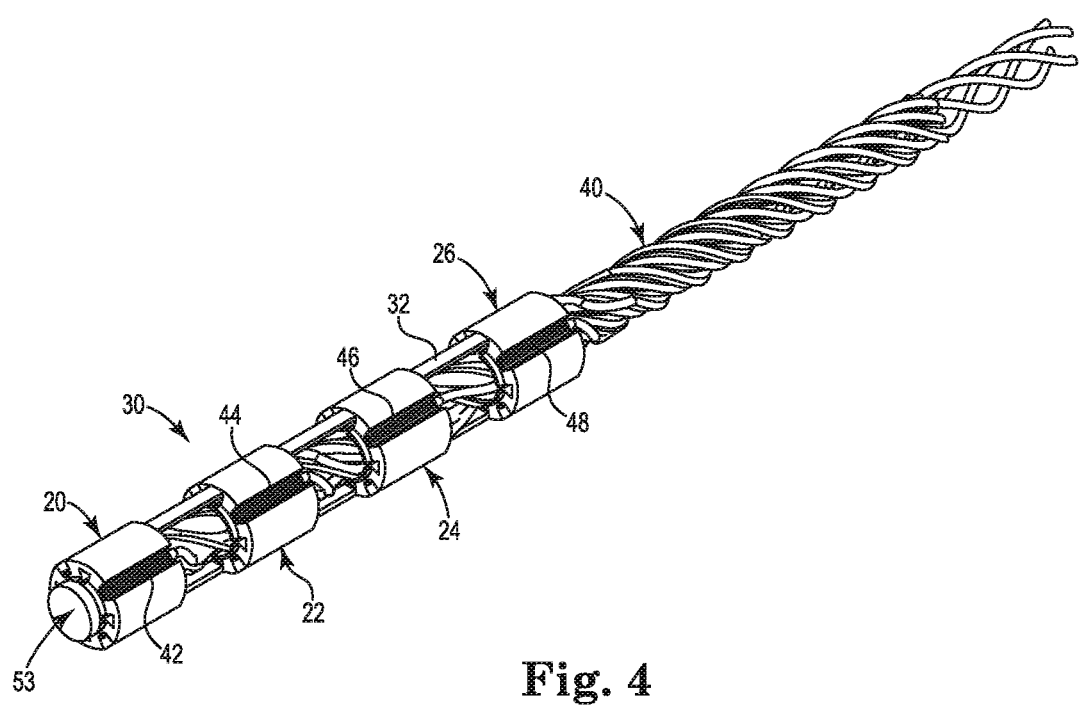
FIG. 4 illustrates a perspective view of an electrode assembly with wiring for a lead in accordance with one embodiment.

FIG. 4 illustrates strut 50 assembled within electrode assembly 30. In one embodiment, strut 50 is provided with a stop 53 and a plurality of helical channels 52. During assembly, strut 50 is inserted into electrode assembly 30 up to stop 53, such that stop 53 is adjacent electrode 20 as illustrated in FIG. 4. Stop 53 ensures proper axial alignment of strut 50 within electrode assembly 30, such that the length of strut 50 extends within each of electrodes 20, 22, 24, 26 and supports the plurality of flexible conductors 40 therein. In one embodiment, strut 50 is also provided with a center lumen 51, illustrated in FIG. 5, where stop 53 is removed to reveal center lumen 51 and the plurality of helical channels 52 in the end view.

In one embodiment where 16 flexible conductors make up the plurality of flexible conductors 40, four helical channels 52 are provided in strut 50. In this way, each flexible conductor 42, 44, 46, 48 that is coupled to a groove 20b, 22b, 24b, 26b is then placed into a helical channel 52 of strut 50.

Each channel 52 is configured to accommodate up to four flexible conductors. For example, each of the four flexible conductors 42 coupled within the four grooves 20b of first electrode 20 are each placed in one of the four channels of strut 50. Then, moving down the length of electrode assembly 30, four more flexible conductors 44 that are coupled within the four grooves 22b of second electrode 22 are each placed in one of the four channels of strut 50 adjacent the flexible conductors from second electrode 22. Again, moving down the length of electrode assembly 30, four more flexible conductors 46 that are coupled within the four grooves 24b of third electrode 24 are each placed in one of the four channels of strut 50 adjacent the flexible conductors from first and second electrodes 20 and 22. Finally, once flexible conductors 48 are coupled to fourth electrode 24, there will be four flexible conductors in each of the four channels 52 of strut 50. As such, each of the flexible conductors are well supported during subsequent molding processes and during use of lead 10.

Figure 5:
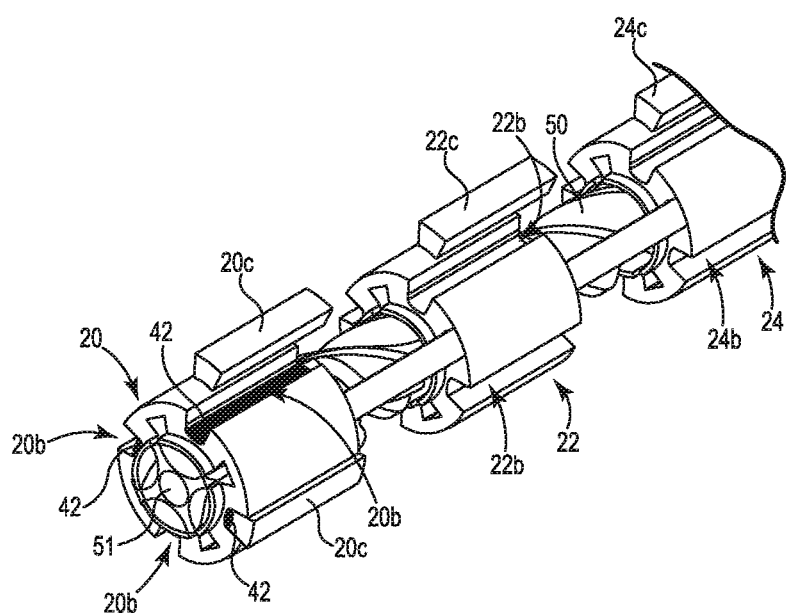
FIG. 5 illustrates a partial perspective view of an electrode assembly with wiring for a lead in accordance with one embodiment.

In one embodiment, the plurality of flexible conductors 40 are secured to electrodes 20, 22, 24, 26 using wedges 20c, 22c, 24c, 26c, as illustrated in FIG. 5 (not all wedges are shown for simplification of the figure). Once a flexible conductor is placed in a groove, such as groove 20b illustrated in FIG. 5, wedge 20c is then placed within groove 20b over the flexible conductor 42, thereby securing flexible conductor 42. In one embodiment, wedge 20c is of the same material as electrode 20 and can be resistance or laser welded into place.

Because the plurality of flexible conductors 40 are supported by strut 50 and secured to electrodes 20, 22, 24, 26, flexible conductors are wires or cables that are flexible and easily threaded up into electrodes 20, 22, 24, 26, thereby simplifying the manufacturing process. In some previous designs, hypotubes, or stiff metal tubes were welded to the inner periphery of electrodes. Using the stiff metal tubes complicates both the assembly and the welding process.

Figure 6A:
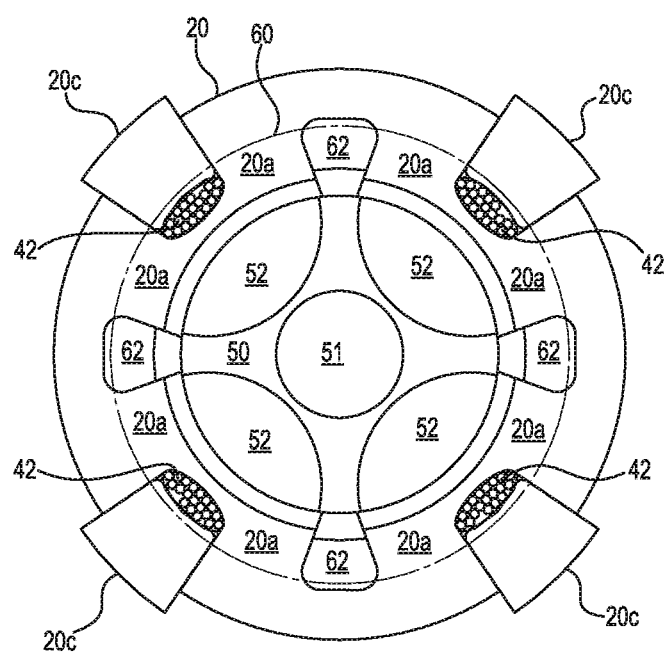
FIG. 6A illustrates an end view of an electrode assembly with wiring before centerless grinding in accordance with one embodiment.

FIG. 6A illustrates an end view of first electrode 20 with wedges 20c secured within each of four grooves 20b on the outer periphery of electrode 20. Flexible conductors 42 are illustrated firmly secured under each of wedges 20c. Strut 50 is also illustrated within electrode 20. For illustration purposes, stop 53 is removed so that four helical channels 52 are illustrated, each one for supporting one of the four flexible conductors 42 secured within grooves 20b. Strut 50 supporting the plurality of flexible conductors 40 in this way minimizes strain on the flexible conductors and secures during subsequent molding processes, as will be further discussed.

Once each of flexible conductors 42 are secured within grooves 20b, electrode 20 is then ground from its outer periphery inward to grind line 60 in order to define electrode segments 20a. In one embodiment, a centerless grinding process is used to grind down to grind line 60. In its original configuration as part of electrode assembly 30, electrode 20 includes openings 62 along its inner periphery. As electrode 20 is ground down to grind line 60, openings 62 are then exposed in the post-grind outer periphery of electrode 20, thereby defining electrode segments 20a.

Figure 6B:
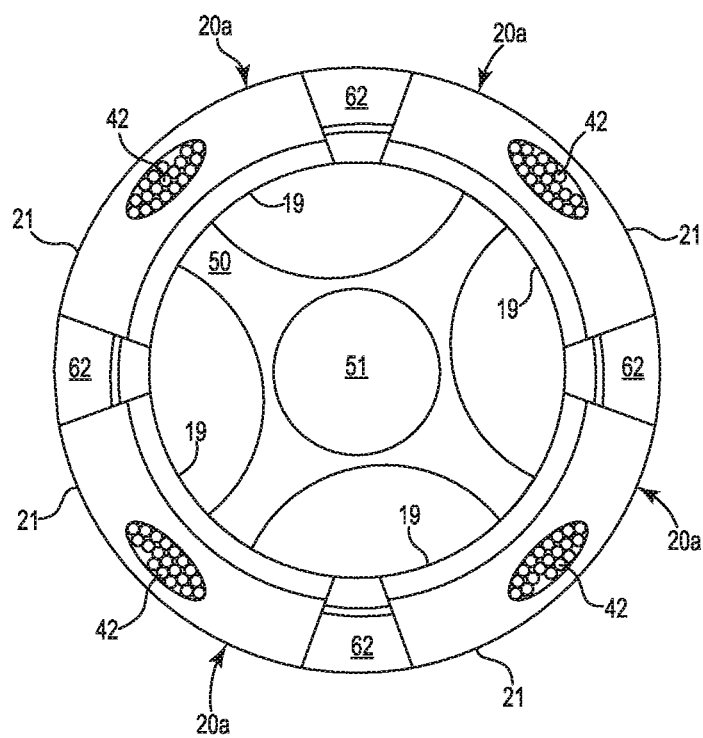
FIG. 6B illustrates an end view of an electrode assembly with wiring after centerless grinding in accordance with one embodiment.

FIG. 6B illustrates electrode 20 after the grinding process. For each of electrode segments 20a defined between openings 62, flexible conductors 42 are embedded and secured between the outer periphery 21 and inner periphery 19 of electrode segments 20a. Furthermore, each electrode segment 20a is electrically isolated from each other segment by opening 62 and can be individually accessed via each of the four flexible conductors 42. FIGS. 6A and 6B illustrate the processing of electrode 20 before and after grinding, but processing the other electrodes 22, 24 and 26 is directly analogous. The number of openings 62 provided in the electrodes 20, 22, 24, 26 of electrode assembly 30 determines the number of electrode segments that will be defined after grinding. Although four openings are illustrated, two, three, four or five openings can be provided to respectively define two, three, four or five electrode segments 20*a*. The number of flexible conductors 42 provided also matches the number of electrode segments 20*a* so that each can be independently accessed.

Figure 7A:
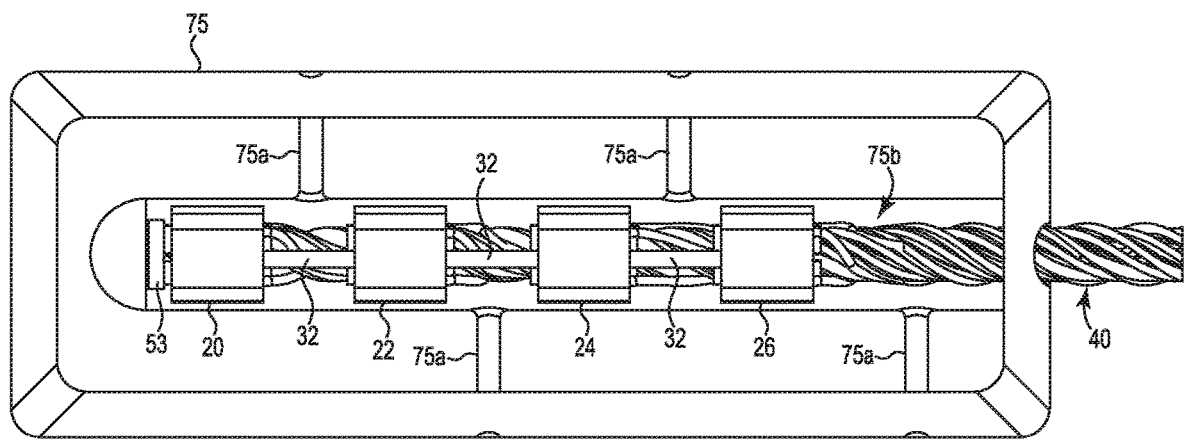
FIG. 7A illustrates a top view of an electrode assembly with wiring for a lead in a mold cavity in accordance with one embodiment.

In one embodiment, the centerless grinding process can be done before the electrode assembly is molded, and in another embodiment, the centerless grinding process is done after the assembly is molded. FIG. 7A illustrates the later embodiment, where strut 50 assembled within electrode assembly 30 and coupled to the plurality of flexible conductors 40 (such as illustrated in FIG. 4), is placed within injection mold 75. Injection mold 75 includes mold cavity 75*b*, in which electrode assembly 30 is placed, and mold gates 75*a*. Once mold cavity 75*b* is closed against its mirror image cavity (not illustrated), molding material, such as thermoplastic or elastomer insulation, is flowed into cavity 75*b* via mold gates 75*a*. The mold material fills all spaces within electrode assembly 30, including filing around the combination of strut 50 and the plurality of flexible conductors 40 between each of the electrodes 20, 22, 24, 26, and also filing any small spaces within each of electrodes 20, 22, 24, 26. Because the plurality of flexible conductors 40 are supported within strut 50, they are not significantly disturbed by the force with which the mold material enters cavity 75*b*, and are instead supported and held in place between strut 50 and within each of electrodes 20, 22, 24, 26.

After the mold material solidifies, the entire assembly is removed and centerless ground to form lead 10, as illustrated in FIG. 1. Molding material fills the spaces between each of electrode segments 20*a*, 22*a*, 24*a*, 26*a* such that each is electrically isolated from each other by the insulative molding material. Each of the plurality of flexible conductors 40 are surrounded and firmly secured with the molding material.

When an elastomer is used as the mold material, lead 10 has some flexibility, which is useful in some applications, such as where lead 10 is incorporated into a catheter configured to navigate the tortuous vasculature of a human body. In such case, the helical configuration of the strut 50, with the plurality of flexible conductors 40 following the helical configuration, allows relief to the flexible conductors as the lead 10 bends as it moves through the vasculature. If the flexible conductors are all aligned parallel, rather than twisted around the helical configuration, too much bending can cause too much strain on the flexible conductors.

Figure 7B:
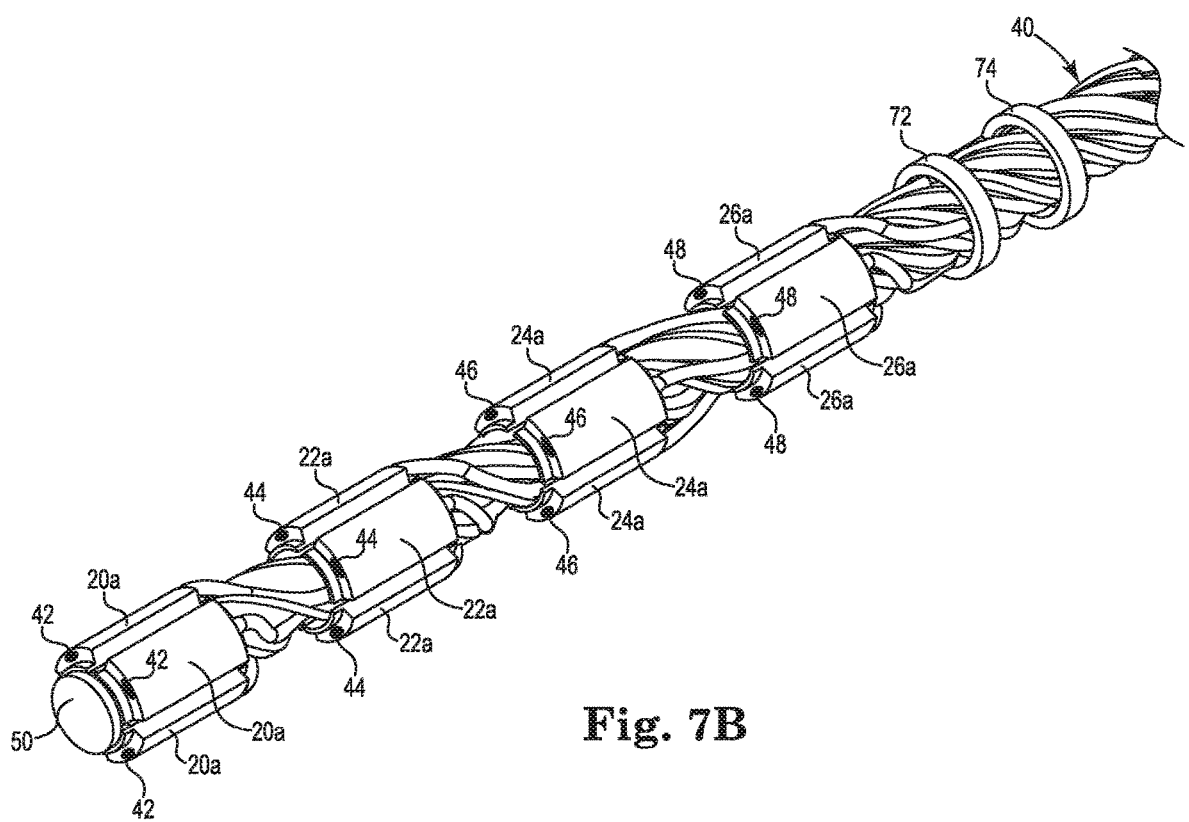
FIG. 7B illustrates a perspective view of an electrode assembly with wiring for a lead after grinding in accordance with one embodiment.

FIG. 7B illustrates further processing of lead 10 in accordance with one embodiment. As illustrated, each of electrodes 20, 22, 24, 26 have been ground to define a plurality of electrode segments 20*a*, 22*a*, 24*a*, 26*a* (four segments in the illustrated example, although only three are visible in the view). Four each of flexible conductors 42, 44, 46, 48 are respectively embedded in electrode segments 20*a*, 22*a*, 24*a*, 26*a* such that the plurality of flexible conductors 40 include a total of 16. Each of the plurality of flexible conductors 40 are secured within the helical channels 52 of strut 50. In order to further illustrate the internal portions of lead 10, all molding material has been removed from the illustration.

With the centerless grinding process, in addition to removing an outer periphery of each of electrodes 20, 22, 24, 26, the grinding also removes each of the coupling segments 32 between the electrodes. The axial location of each of the electrodes relative to each other, however, is maintained by strut 50, which is secured within electrode assembly 30 before the grinding process. Strut 50 within electrode assembly 30 is configured to extend through each of electrodes 20, 22, 24, 26 and thereby constrain the axial distance and axial orientation of each of the electrodes 20, 22, 24, 26 even after the coupling segments 32 have been ground away.

In one embodiment, lead 10 also includes marker bands 72 and 74. Marker bands are useful in locating lead 10 once inserted in a human body via magnetic imaging. Accordingly, by locating the marker bands, the axial location and orientation of the electrode segments 20*a*, 22*a*, 24*a*, 26*a* can be determined.

Figure 8:
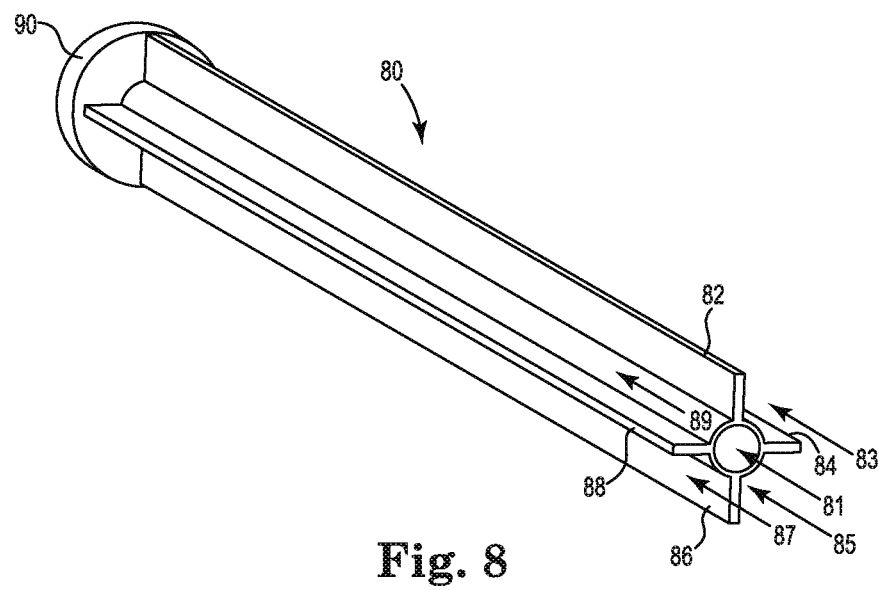
FIG. 8 illustrates a perspective view of a strut for a lead in accordance with one embodiment.

FIG. 8 illustrates strut 80 in accordance with one embodiment. Strut 80 is analogous to strut 50 illustrated in FIG. 4. In one embodiment, strut 80 includes a stop 90, a center lumen 81, and four ribs 82, 84, 86, 88, thereby defining four channels 83, 85, 87, 89, each channel defined between two adjacent ribs. In one embodiment, multiple flexible conductors from a plurality of flexible conductors 120 can be placed in each channel 83, 85, 87, 89, in order to support and maintain the position of the flexible conductor, and isolate flexible conductors in one channel from those in other channels.

Figure 9:
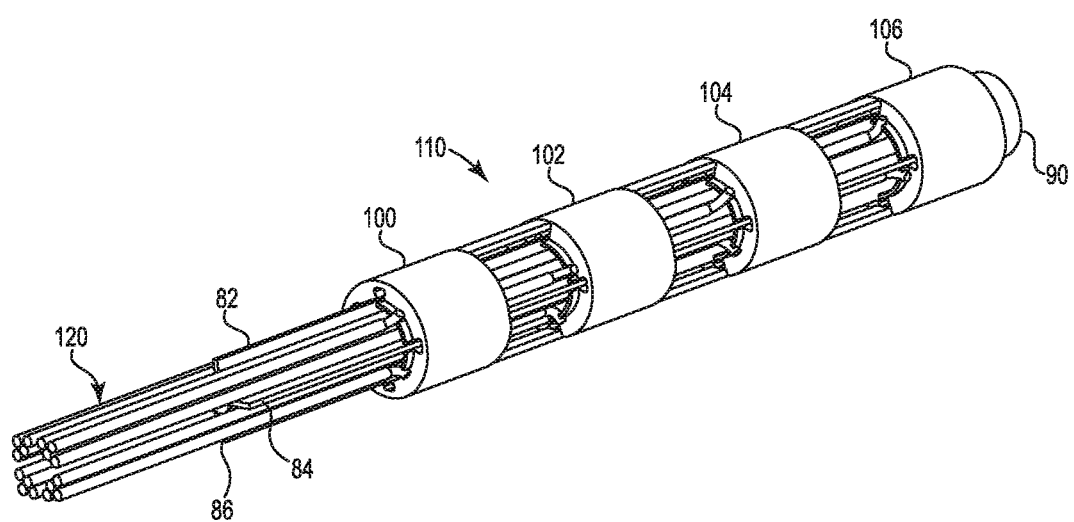
FIG. 9 illustrates a perspective view of an electrode assembly with wiring for a lead in accordance with one embodiment.

FIG. 9 illustrates an electrode assembly 110 coupled over strut 80 with a plurality of flexible conductors 120 coupled thereto. As with the electrode assembly 30 previously described, electrode assembly 110 includes first, second, third and fourth electrodes 100, 102, 104, 106, which are coupled over strut 80. In one embodiment, each of electrodes 100, 102, 104, 106 will be segmented with a centerless grinding process to form four electrode segments each. In other embodiments, two, three or five segments are possible for each electrode. In the illustrated embodiment with four electrode segments, each electrode 100, 102, 104, 106 couple with four flexible conductors—one connected to each of its segments, as will be more fully described. As such, strut 50 accommodates four flexible conductors in each of its four channels 83, 85, 87, 89 between each of its four ribs 82, 84, 86, 88, thereby supporting the plurality of flexible conductors 120 between strut 80 and electrodes 100, 102, 104, 106.

During assembly, strut 80 is inserted into electrode assembly 110 up to stop 90, such that stop 90 is adjacent electrode 106 as illustrated in FIG. 9. Stop 90 ensures proper axial alignment of strut 80 within electrode assembly 110, such that the length of strut 80 extends within each of electrodes 100, 102, 104, 106 and supports the plurality of flexible conductors 120 therein, and separates them into channels 83, 85, 87, 89. In one embodiment, strut 80 is also provided with a center lumen 81, illustrated in FIG. 8.

Figure 10:
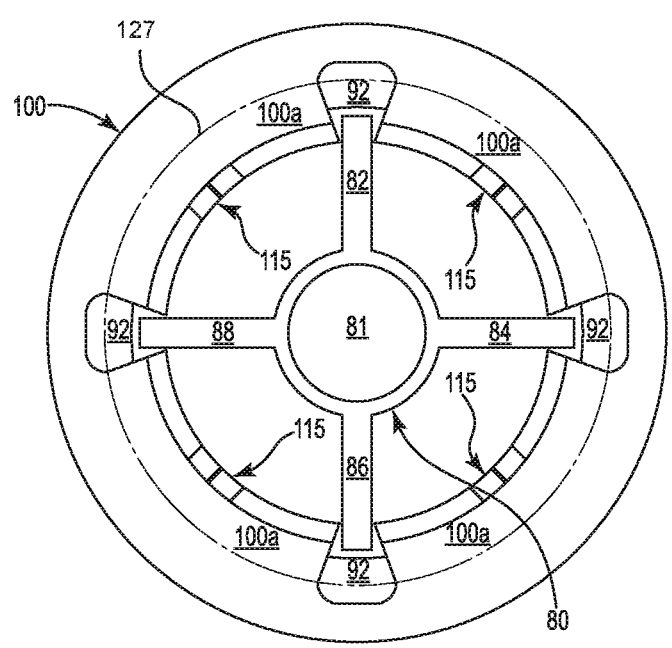
FIG. 10 illustrates an end view of an electrode assembly before centerless grinding in accordance with one embodiment.

FIG. 10 illustrates an end view of the electrode assembly 110 and strut 80 from FIG. 9. Electrode 100 includes openings 92. In one embodiment, four openings 92 are provided so that four electrode segments 110*a* are defined by the grinding process. As previously described relative to electrode assembly 30 and strut 50, electrode assembly 110 and strut 80 are ground from the periphery down to grind line 127. This grinding exposes openings 92, thereby defining electrode segments 100*a*, each of which are electrically isolated from each other by openings 92. Each on openings 92 are filled with molding material by the molding process described above relative to electrode assembly 30.

Electrode 100 also includes notches 115. Notches 115 provide a flexible conductor retaining feature, analogous to that provided by grooves 20b, 22b, 24b, 26b in electrode assembly 30, which facilitates attaching one flexible conductor of the plurality of flexible conductors 120 to each electrode segment 100a.

Figure 11:
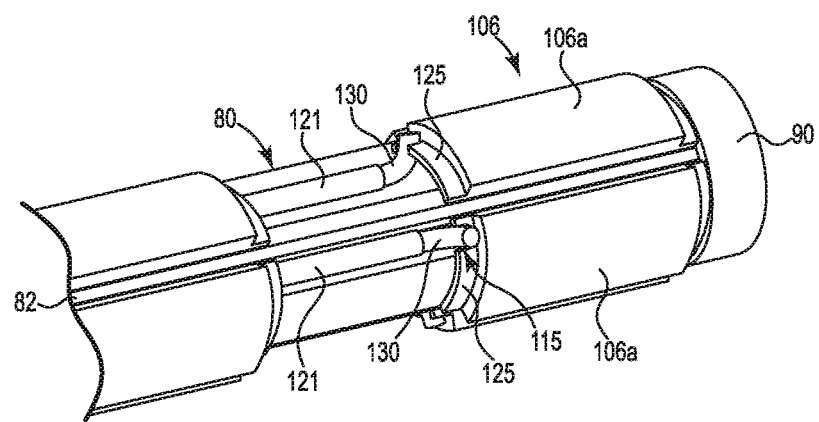
FIG. 11 illustrates a partial perspective view of an electrode assembly with wiring for a lead in accordance with one embodiment.

FIG. 11 illustrates a more detailed view of a portion of electrode assembly 110, and connections between the plurality of flexible conductors 120 and electrode segments 106a. The electrode assembly 110 illustrated is after a grinding process, such that electrode segments 106a have been defined, and molding material is either not yet added or has been removed for illustration purposes. Each electrode segment 106a includes a shoulder 125. Notches 115 are provided in shoulder 125 for each electrode segment 106a. Accordingly, four flexible conductors 121 of the plurality of flexible conductors 120 are attached to the four notches 115, one for each of the four electrode segments 106a.

In one embodiment, each flexible conductor 121 includes a bend at its end 130, such that it is more readily inserted into notch 115 and can easily be welded into place. In one embodiment, the bend at end 130 is approximately 90 degrees. Flexible conductors 121 are fed through channels 83, 85, 87, 89 and up to one of the electrodes. The bend at the flexible conductor end 130 is then placed into notch 115 and welded there, for example, resistance or laser welded. As illustrated in FIG. 11, each flexible conductor 121 coupling to each electrode segment 106a is in a separate channels 83, 85, 87, 89, and thus, separated from each other by a rib 82, 84, 86, 88. This affords management of the plurality of flexible conductors 120 and streamlines the assembly process and avoids confusing flexible conductors 121. Furthermore, each of the flexible conductors are well supported during subsequent molding processes and during use of lead 10.

Once all flexible conductors are attached to electrode segments 100a, 102a, 104a, 106, the assembly is placed in a mold, such as mold 75 in FIG. 7A and overmolded as previously described. After the mold material solidifies, the entire assembly is removed and centerless ground to form lead 10, as illustrated in FIG. 1. As with previous designs, the centerless grinding process can be done before the electrode assembly is molded, or the centerless grinding process may be done after the assembly is molded.

Figure 12:
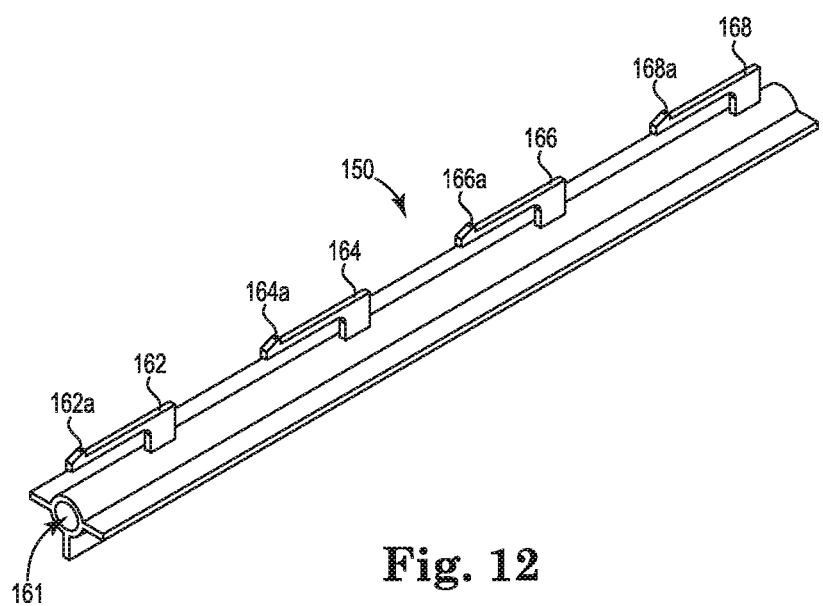
FIG. 12 illustrates a perspective view of a strut for a lead in accordance with one embodiment.

FIG. 12 illustrates strut 150 in accordance with one embodiment. Strut 150 is analogous to struts 50 and 80 previously described and can be used in any of the previous embodiments. In one embodiment, strut 150 further includes positioning arms 162, 164, 166, 168. Each positioning arm is configured with a catch 162a, 164a, 166a, 168a. Strut 150 may be used as strut 50 or 80 described previously, but also provide additional positioning of electrodes. For example, any of electrode 20, 22, 24, 26 in FIG. 2 can be fed over strut 150 and snapped into place via positioning arms 162, 164, 166, 168 and catches 162a, 164a, 166a, 168a. First electrode 20 can be moved over each of the positioning arms 162, 164, 166, 168 and snapped into place in fourth positioning arm 168. Catch 168a will then engage a feature in electrode 20 such that it cannot be moved back in the direction from which it was assembled. The next three electrodes 22, 24, 26 can be assembled over the three remaining positioning arms 162, 164, 166 in the same way.

In preventing back movement of each electrode, positioning arms 162, 164, 166, 168 and catches 162a, 164a, 166a, 168a ensure that each electrode is precisely positioned along the length of strut 150 correctly and ensures that the relative distance between each electrode is precisely controlled. This is important in many applications where positioning of the electrode segment relative to tissue in the human body must be very precise. Also, catches 162a, 164a, 166a, 168a preventing backward movement along the length of strut 150 is useful during the injection molding process. Even where significant flow forces are generated by molten molding material moving into the mold cavity, catches 162a, 164a, 166a, 168a prevent electrodes from being moved axially by these forces.

Figure 13:
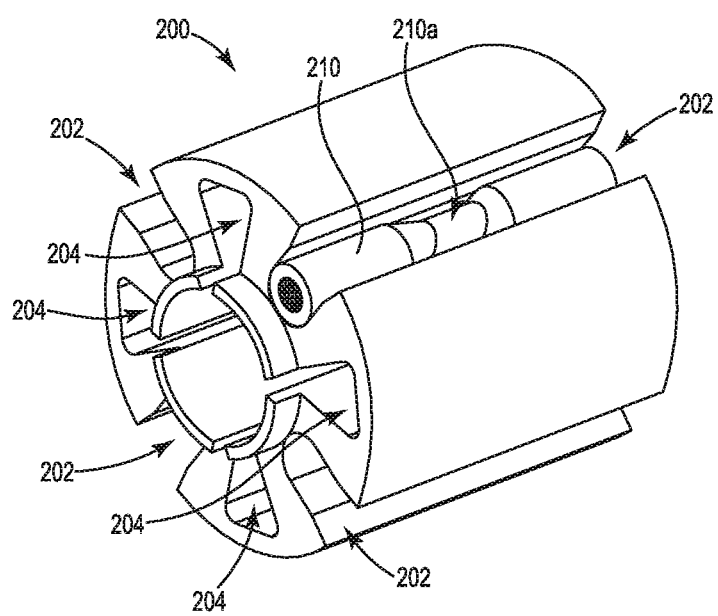
FIG. 13 illustrates a perspective view of an electrode from an electrode assembly for a lead in accordance with one embodiment.

FIG. 13 illustrates an electrode 200 in accordance with one embodiment. Electrode 200 is analogous to those previously described and can be used in any of the previous embodiments. Electrode 200 includes grooves 202 and openings 204. In the Figure, four grooves 202 and openings 204 are illustrated, but other amounts, for example, two, three or five, are possible. In each groove 202, sleeve 210 is provided over a flexible conductor. Sleeve 210 helps facilitate a good connection between the plurality of flexible conductors 40, 120 and electrode 200.

Although only a single sleeve 210 is illustrated in FIG. 13 for ease of illustration, in assembly of lead 10 a sleeve 210 is inserted in each of the four grooves 202. In one embodiment, each flexible conductor is inserted into a sleeve 210 and then a crimp 210a is made on sleeve 210 to secure the flexible conductor within sleeve 210. Once the flexible conductor is secure within sleeve 210, sleeve 210 is placed within groove 202 and can be welded into place. In one embodiment, sleeve 210 is welded at each of its ends.

Figure 14:
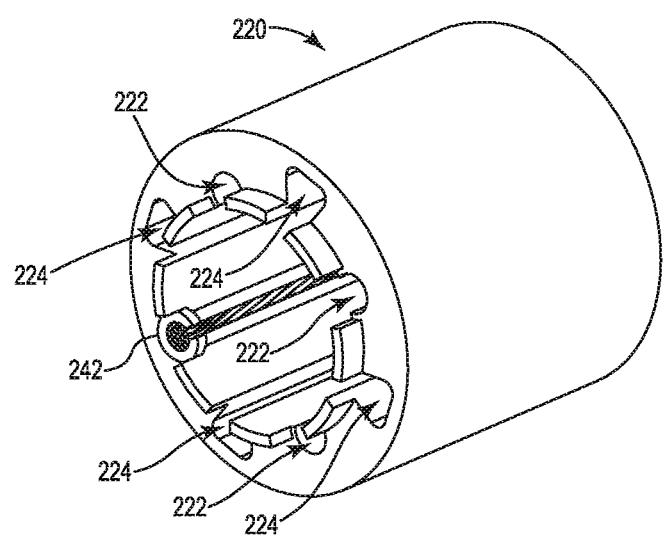
FIG. 14 illustrates a perspective view of an electrode from an electrode assembly for a lead in accordance with one embodiment.

FIG. 14 illustrates an electrode 220 in accordance with one embodiment. Electrode 220 is analogous to those previously described and can be used in any of the previous embodiments. Electrode 220 includes grooves 222 and openings 224. In the Figure, four grooves 222 and openings 224 are illustrated, but other amounts, for example, two, three or five, are possible. In each groove 222, sleeve 242 is provided over a flexible conductor. Sleeve 242 helps facilitate a good connection between the plurality of flexible conductors 40, 120 and electrode 220.

Although only a single sleeve 242 is illustrated in FIG. 14 for ease of illustration, in assembly of lead 10 a sleeve 242 is inserted in each of the four grooves 222. In one embodiment, each flexible conductor is inserted into a sleeve 242 and then a crimp is made on sleeve 242 to secure the flexible conductor within sleeve 242. Once the flexible conductor is secure within sleeve 242, sleeve 210 is slid into groove 222 and can be welded into place. In one embodiment, sleeve 242 is welded at its end.

Figure 15:
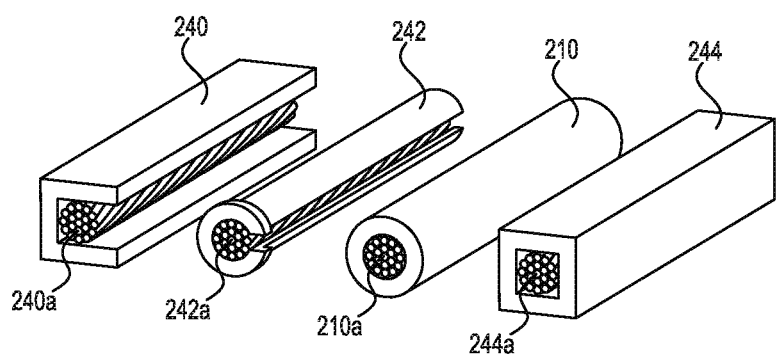
FIG. 15 illustrates perspective views of wire sleeves for use in an electrode for a lead in accordance with one embodiment.

FIG. 15 illustrates various embodiments of sleeves 210, 240, 242, 244 over flexible conductors 210a, 240a, 242a, 244a for use in the electrodes previously described. As illustrated, sleeves 210, 240, 242, 244 for use in electrodes, such as electrodes 200, 220 illustrated in FIGS. 13-14, can be of various configurations. Sleeve 210 is generally cylindrical and over flexible conductor 210a, similar to that illustrated in groove 202 of FIG. 13. Sleeve 242 is also generally cylindrical with a longitudinal slot along its length. Sleeves 240 and 244 are generally rectangular, sleeve 244 being closed and sleeve 240 has an open slot. Each of sleeves 210, 240, 242, 244 can include a crimp over flexible conductors 210a, 240a, 242a, 244a to ensure the respective sleeve tightly retains the flexible conductor. Each sleeve can then be welded into the respective groove of an electrode.

Figure 16A:
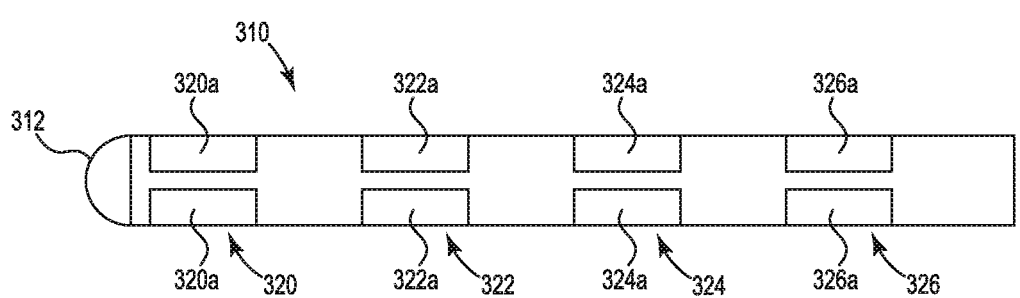
FIGS. 16A-16B illustrate side and perspective views of a lead with segmented electrodes in accordance with one embodiment.
Figure 16B:
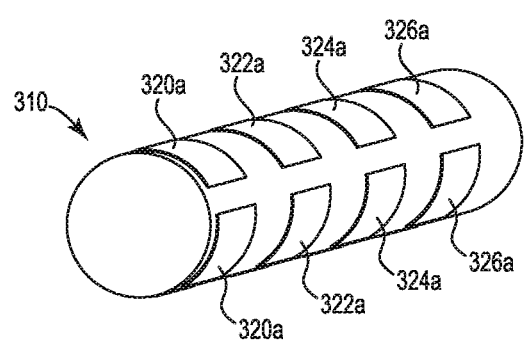

FIGS. 16A and 16B illustrate side and perspective views of lead 310 in accordance with one embodiment. Lead 310 includes four electrodes 320, 322, 324, 326 out toward its distal tip 312. Each of the four electrodes 320, 322, 324, 326 are segmented such that each has independently accessible electrode segments 320a, 322a, 324a, 326a. In the illustrated embodiment, each of the electrode segments 320a, 322a, 324a, 326a are radially aligned. For example, each electrode segment 320a of electrode 320 is aligned with each electrode segment 322a (and the other segments 324a, 236a), such that their edges lie on a continuous straight line along the length of lead 310. This configuration may be useful in certain application for ensuring proper location of the electrode segments relative to tissue that is being stimulated or sensed.

Figure 17A:
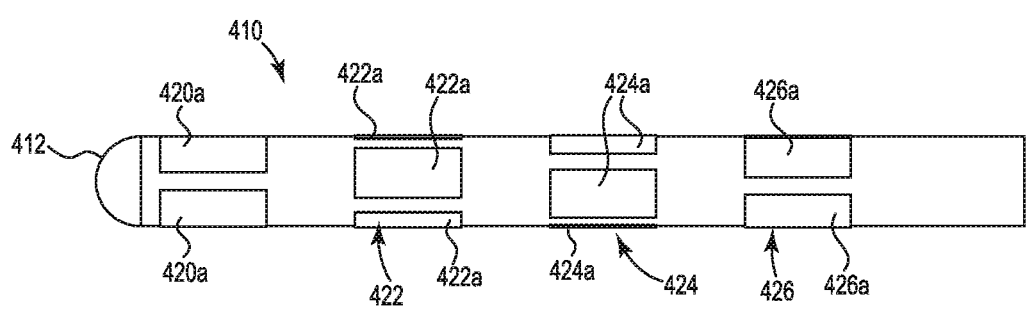
FIGS. 17A-17B illustrate side and perspective views of a lead with segmented electrodes in accordance with one embodiment.
Figure 17B:
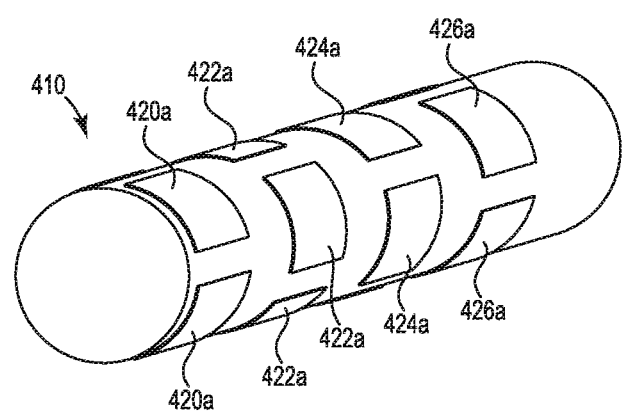

FIGS. 17A and 17B illustrate side and perspective views of lead 410 in accordance with one embodiment. Lead 410 includes four electrodes 420, 422, 424, 426 out toward its distal tip 412. Each of the four electrodes 420, 422, 424, 426 are segmented such that each has independently accessible electrode segments 420a, 422a, 424a, 426a. In the illustrated embodiment, each of the electrode segments 420a, 422a, 424a, 426a are radially offset. For example, each electrode segment 420a of electrode 420 is radially rotated slightly relative to each electrode segment 422a (and the other segments 324a, 236a), such that none of their edges lie in a straight line along the length of lead 310. This configuration may be useful in certain application for accessing certain locations of the electrode segments relative to tissue that is being stimulated or sensed.

Figure 18:
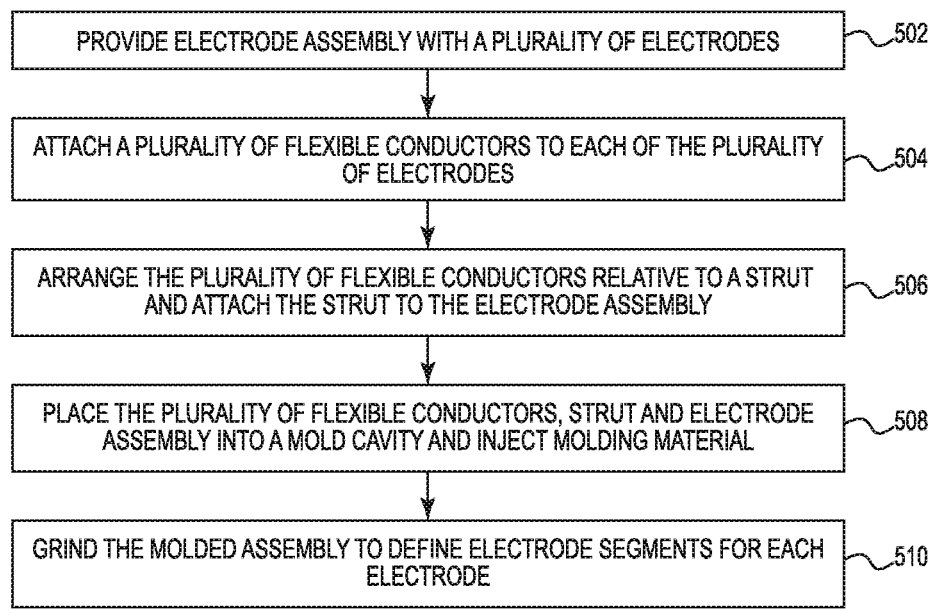
FIG. 18 illustrates a method of forming a medical lead with segmented electrodes in accordance with one embodiment.

FIG. 18 illustrates a method of forming a segmented electrode lead, such as leads 10, 310 and 410 in accordance with one embodiment. First, at step 502, an electrode assembly, such as previously described is formed. The electrode assembly may be formed by any of a variety of processing, including machining, metal injection molding, 3-D printing and/or metal screen printing. The formed electrode assembly has a plurality of electrodes, for example, two, three, four or five. In one embodiment, each of the electrodes in the electrode assembly are each configured with opening and grooves. The grooves are useful in coupling conductors and the openings will define electrode segments.

At step 504, a plurality of flexible conductors are attached to each of the plurality of electrodes. In one embodiment, a single flexible conductor is attached to each portion of each electrode that will be formed into an electrode segment. For example, if an electrode will be formed into three electrode segments, then three flexible conductors will be attached to that electrode, one flexible conductors connected at each of the segments. In one embodiment, a single flexible is coupled in each groove provided in the electrodes.

At step 506, the plurality of flexible conductors are arranged relative to a strut. In some embodiments, the flexible conductors are helically wrapped in channels of the strut. In other embodiments, the flexible conductors are sorted into separate channels of the strut. Once the flexible conductors are arranged, the strut is inserted into the electrode assembly, such that the strut is within each of the electrodes in the assembly.

At step 508, the combination of the flexible conductors, the strut and the electrode assembly are placed into a mold cavity, and molding material is injected into the cavity. Gaps between the flexible conductors, the strut and the electrode assembly are filled with the molding material, which is allowed to solidify.

At step 510, the molded electrode assembly is ground inward from its outer periphery. In one embodiment, a centerless grinding process is used to grind the molded electrode assembly down to a grind line that exposed the openings that are formed in each electrode. In so doing, each electrode is segmented, such that a plurality of electrode segments are defined wherein each is electrically isolated from each other.

The various described steps are not necessarily required in a particular order. For example, a centerless grinding process may be applied to the combination of the flexible conductors, the strut and the electrode assembly before the combination is placed into a mold cavity. The injection molding process can then be the last step in producing the finished lead.

Although specific embodiments have been illustrated and described herein, it will be appreciated by those of ordinary skill in the art that a variety of alternate and/or equivalent implementations may be substituted for the specific embodiments shown and described without departing from the scope. This application is intended to cover any adaptations or variations of the specific embodiments discussed herein. Therefore, it is intended that these embodiments be limited only by the claims and the equivalents thereof.

What is claimed is:

1. A medical lead for implantation comprising:
an electrode assembly comprising a plurality of electrodes;
wherein each of the plurality of electrodes comprise a plurality of electrode segments and wherein each electrode segment has a groove and a flexible conductor directly coupled in the groove;
a strut having channels and coupled within the plurality of electrodes such that each of the flexible conductors coupled to the plurality of electrode segments are supported by the channels of the strut; and
an insulator filling gaps between the plurality of electrodes, the strut and the flexible conductors;
wherein at least one electrode segment comprises a wedge configured to hold the flexible conductor against the groove of the at least one electrode segment thereby securing the flexible conductor between the wedge and the at least one electrode segment, wherein centerless grinding of the electrode assembly exposes openings between the plurality of electrode segments and exposes at least a portion of the wedge on an outer surface of the at least one electrode segment; and
wherein the wedge and the at least one electrode segment are of the same material.

2. The medical lead of claim 1, wherein each electrode segment comprises an inner and an outer periphery and wherein no part of the flexible conductor is attached to either the inner or outer periphery.

3. The medical lead of claim 1, wherein the lead contains no hypotubes and wherein the strut is configured to extend through each one of the plurality of electrodes.

4. The medical lead of claim 1, wherein the plurality of electrode segments comprise a feature configured to receive the flexible conductor and to secure the flexible conductor to the electrode segment.

5. The medical lead of claim 1, wherein the strut comprises a stop configured to engage the electrode assembly and ensure proper relative positioning of the strut and electrode assembly.

6. The medical lead of claim 1, wherein the electrode assembly comprises between two and four electrodes and wherein each electrode comprises between two and five electrode segments.

7. The medical lead of claim 1, wherein the strut further comprises positioning arms configured to receive and space the electrodes relative to each other.

8. The medical lead of one of claim 7, wherein the positioning arms are further configured with stops to prevent movement of the electrodes in at least one axial direction.

9. The medical lead of claim 1 further comprising sleeves configured over the flexible conductors and within the grooves of the electrodes.

10. The medical lead of claim 9, wherein the sleeves are crimped over the flexible conductors and are rectangular or cylindrical shaped.

11. The medical lead of claim 1, wherein the segmented electrodes are one of axially aligned and axially offset.

12. A method of manufacturing a medical lead comprising:
   manufacturing an electrode assembly comprising a plurality of electrodes;
   forming a plurality of grooves in each of the plurality of electrodes;
   coupling a flexible conductor directly within each groove of the plurality of grooves in each of the plurality of electrodes, including securing a wedge over the flexible conductor and against each groove thereby securing the flexible conductor between the wedge and each groove;
   configure the flexible conductors to a strut and attach the strut to the plurality of electrodes; and
   fill gaps between the plurality of electrodes, the strut and the flexible conductors with an insulator material; and
   forming a plurality of electrode segments comprising centerless grinding the plurality of electrodes down to a grind line thereby exposing openings between adjacent electrode segments and exposing at least a portion of the wedge and wherein the wedge and the at least one electrode segment are of the same material.

13. The method of claim 12 further comprising inserting the strut up to a stop such that the strut extends through each one of the plurality of electrodes.

14. The method of claim 12 further comprising feeding the flexible conductors though a plurality of channels in the strut, wherein the electrodes are spaced relative to each on the strut using positioning arms on the strut and further comprising sliding sleeves over the flexible conductors and within the grooves of the electrodes.

* * * * *